United States Patent [19]

Rovnyak

[11] 4,325,958
[45] Apr. 20, 1982

[54] BIS-AMIDINE KETONES, COMPOSITIONS CONTAINING SAME AND METHOD OF USE

[75] Inventor: George C. Rovnyak, Hopewell, N.J.

[73] Assignee: E. R. Squibb & Sons, Inc., Princeton, N.J.

[21] Appl. No.: 270,774

[22] Filed: Jun. 5, 1981

[51] Int. Cl.³ .................. A61K 31/35; A61K 31/38; C07D 309/38; C07D 335/02
[52] U.S. Cl. .................... 424/267; 424/275; 424/283; 542/441; 542/442
[58] Field of Search ............... 542/441, 442; 424/267, 424/275, 283

[56] References Cited
PUBLICATIONS

"Synthese von a,a'-Bis-[amidinobenzyliden]-und a,a'-Bis-[amidinobenzyl]-cycloalkanonen", Wagner et al, Pharmazie 32, pp. 141-145 (1977).

Primary Examiner—Richard Raymond
Attorney, Agent, or Firm—Lawrence S. Levinson; Burton Rodney

[57] ABSTRACT

Bis-amidine ketones are provided having the structure

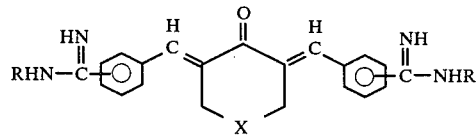

wherein X is S, $SO_2$, O or $NR^1$; R is hydrogen, lower alkyl or aryl; and $R^1$ is hydrogen, lower alkyl, acyl, aroyl or aryl-lower alkyl, and acid-addition salts thereof. In addition, pharmaceutical compositions containing the above compounds and a method of using same to treat inflammatory conditions in mammalian species are also provided.

10 Claims, No Drawings

BIS-AMIDINE KETONES, COMPOSITIONS CONTAINING SAME AND METHOD OF USE

FIELD OF THE INVENTION

The present invention relates to bis-amidine ketones, anti-inflammatory compositions containing same, and to a method for treatment of inflammatory conditions employing the above compounds.

DESCRIPTION OF THE INVENTION

The bis-amidine ketones of the invention have the following formula

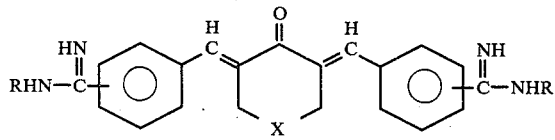

I wherein X is S, $SO_2$, O or $NR^1$ wherein $R^1$ is H, lower alkyl, lower alkanoyl, aroyl, or aryl-lower alkyl, and R is H, lower alkyl, or aryl.

The compounds of Formula I will preferably be in the form of their acid-addition salts with inorganic and organic acids. Illustrative of such acid salts are the hydrohalides, especially the hydrochloride and hydrobromide which are preferred, sulfate, nitrate, phosphate, borate, acetate, tartrate, maleate, citrate, succinate, oxalate, benzoate, ascorbate, salicylate; methanesulfonate, benzenesulfonate, toluenesulfonate and the like.

Preferred are those compounds of Formula I wherein X is S or $SO_2$, R is H or lower alkyl, and the

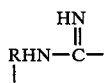

group is in the meta- or para-position of each of the phenyl groups, in the form of their hydrohalide salts, especially the HCl salts.

The terms "lower alkyl" and "lower alkoxy", as used throughout the specification (by themselves or as part of a larger group) refer to groups having 1 to 8 carbon atoms. Alkyl and alkoxy groups having 1 to 3 carbon atoms are preferred.

The term "aryl" as used throughout the specification (by itself or as part of a larger group) refers to phenyl or phenyl substituted with a lower alkyl, lower alkoxy, halogen or trifluoromethyl group. Phenyl is the preferred aryl group.

The term "halogen" as used throughout the specification refers to fluorine, chlorine, bromine, and iodine; fluorine and chlorine are preferred.

The term "lower alkanoyl" as used herein refers to a radical of the structure

wherein $R^2$ is lower alkyl as defined above.

The term "aroyl" as employed herein refers to a radical of the structure

wherein $R^3$ is aryl as defined above.

The Formula I compounds of the invention are prepared by condensing an amidino benzaldehyde II with a ketone III, employing a molar ratio of II:III of from about 2:1 to about 4:1, preferably from about 2.0:1 to about 2.5:1, and optimally about 2:1, using acid catalysis. Although the condensation proceeds in hot (about 100° C.) 85% $H_3PO_4$ and the product can, after isolation, be converted to the hydrohalide salt, the preferred conditions for preparing the compounds of Formula I involve heating the reactants II and III in 5–10% aqueous mineral or other acid, preferably hydrochloric acid, at reflux temperature for one to eight hours, preferably one to two hours. The product I in the form of the amidine acid-addition salt is collected from the cooled solution and can be recrystallized, if necessary, for example, from 0 to 5% aqueous hydrochloric acid.

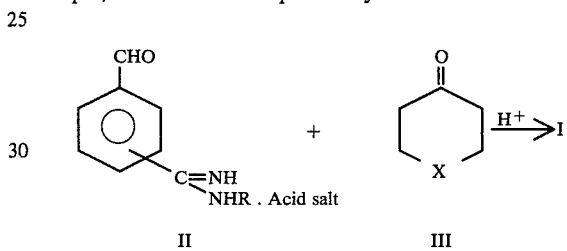

wherein X and R are as defined above with respect to the Formula I compounds.

The compounds of the invention in the form of the free base are prepared as follows.

The amidine acid-addition salt product I, dissolved or suspended in water, is treated with an excess of 10% aqueous sodium hydroxide at or below room temperature and extracted several times with chloroform. The organic extracts are washed with saturated brine, dried over anhydrous magnesium sulfate and concentrated in vacuo to give the free base I. If necessary, the free amidine base can be recrystallized from a suitable solvent (e.g., ethanol, dioxane, benzene, carbon tetrachloride and combinations thereof).

The amidino benzaldehydes II may be prepared by methods reported in East German Pat. No. 109,864 and Pharmazie, 32, 39 (1977). These methods proceed through the intermediate iminoether acid salt, such as hydrochloride IV. In Method A, the iminoether acid salt (hydrochloride) IV is converted to the amidinobenzaldehyde II (where R is H) by reaction with aqueous methanolic ammonium chloride. In Method B, the iminoether acid salt, such as the hydrochloride IV is initially converted to ketal V with triethylorthoformate in methanol. The ketal V is converted to amidine VI with the appropriate amine $NH_2R$ in methanol and the amidine VI is transformed to the amidino benzaldehyde II with aqueous methanolic hydrochloric acid or other acid. Method B is preferred because it allows for the introduction of different R groups.

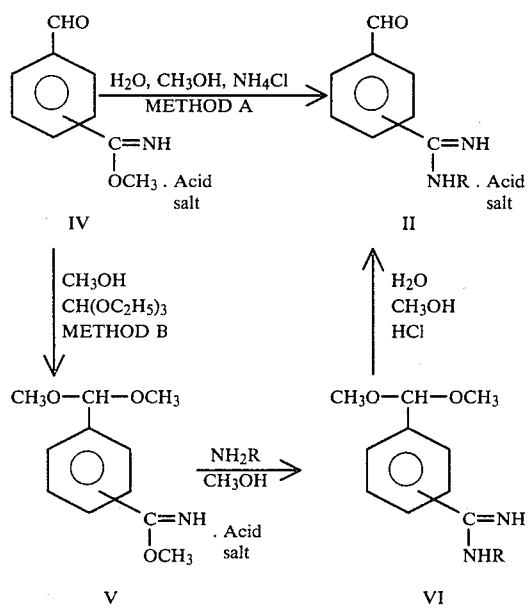

The ketones of Formula III are prepared by known literature methods as described in J. Org. Chem., 33, 4070 (1968) and Synthesis, 509 (1975), CA:54:11019 g.

Amidines are strongly basic compounds and react with acids to form salts, such as hydrochlorides, sulfates, sulfonates, acetates, nitrates, carbonates, etc. [S. R. Sandler and W. Karo, "Organic Functional Group Preparations," Vol. III, Chap. 6, Academic Press, New York (1972)].

The free base I can be combined with an excess, preferably with 2.2 to 3.0 equivalents of the desired acid in an appropriate solvent, such as aqueous ethanol (or acetone, dioxane, etc.) to give the amidine acid-addition salt I.

Alternatively, one amidine acid-addition salt may be converted to another acid-addition salt by mixing with an excess (at least 10–100 fold) of the second acid (or its sodium, potassium or ammonium salt) in an appropriate solvent. For example, the amidine hydrochloride can be mixed with an excess of sodium acetate in warm water (or appropriate solvent mixture) to give the amidine acetate upon cooling [J. Chem. Soc., 1996 (1949)].

The compounds of the invention have anti-inflammatory activity as measured by the mouse active arthus (MAA) test (Goldlust, M. B., Harrity, T. W., and Palmer, D. M., "Evaluation of Anti-Rheumatic Drugs Using the Cutaneous Arthus Reaction," *Recognition of Anti-Rheumatic Drugs, D. C. Dumonde and M. K. Jasani, MTP Press, Lancaster* (1978), pp. 119–136), a Forssman anaphylaxis assay (a variation of the test described by Otterness, Ivan G., Torchia, Anthony J., and Doshan, Harold D., "Complement Inhibition by Amidines and Guanidines—In Vivo and In Vitro Results," Bio Chem. Pharm., Vol. 27, pp. 1873–1878 (1978)) and other related tests and are useful as antiinflammatory agents and are effective in the prevention and inhibition of granuloma tissue formation in warm blooded animals, and may be used, for example, in a manner similar to phenylbutazone or indomethacin. They may be used to decrease joint swelling, tenderness, pain and stiffness in mammalian species, such as dogs and monkeys, e.g., in conditions such as rheumatoid arthritis. Compounds of Formula I may be compounded for such use according to accepted pharmaceutical practice in oral dosage forms, such as tablets, capsules, elixirs or powders or in injectable form for administration of about 100 mg to 2 gm per day, preferably 100 mg to 1 gm per day in two to four divided doses.

The following Examples further illustrate and represent preferred embodiments of the invention. All temperatures are expressed in degrees Centigrade.

EXAMPLE 1

3,3'-[(4-Oxo-2H-thiopyran-3,5-(4H,6H)-diylidene)dimethylidyne]bis[benzenecarboximidamide], hydrochloride (1:2)

A. 3-Amidinobenzaldehyde hydrochloride Ref: Wagner, Vieweg and Horn [Pharmazie, 32, 39 (1977)]

A solution of 3-cyanobenzaldehyde (30 g, 0.23 mole) in dioxane (90 ml), ether (33 ml) and methanol (22.2 g) is treated at 0° (ice bath) with 62 g of HCl gas under anhydrous conditions. Solvents are dried and the HCl gas is passed through two concentrated $H_2SO_4$ drying towers. After 24 hours at 0°–5° the reaction is filtered into 1400 ml of $Et_2O$. The solid that eventually forms is collected, washed with $Et_2O$ and dried in vacuo at 60° over KOH to give 40 g of the iminoether hydrochloride, m.p 108°–110° (lit. m.p 123°–5°).

The iminoether hydrochloride obtained above (6 g, 0.03 mole) is dissolved in ice water, made basic with 10% NaOH and rapidly extracted with $Et_2O$ (2×). The extracts are washed with saturated brine (2×), dried ($MgSO_4$) and concentrated in vacuo to give the free base (4.9 g). This is dissolved in MeOH (25 ml) and 10% aqueous $NH_4Cl$ (18 ml) and heated (100° oil bath) for 3 hours. Upon cooling, the mixture is poured onto $Et_2O$ (300 ml) and the oil that separates is collected and treated with acetone (300 ml). The supernatant is decanted from a tacky solid and concentrated in vacuo to remove all solvent, including residual water. The residue, upon trituration with fresh acetone, affords 3.2 g (57%) of product, m.p. 153°–7° (lit. m.p. 152°–4°).

B. 3,3'-[4-Oxo-2H-thiopyran-3,5-(4H,6H)diylidene)-dimethylidyne]bis[benzenecarboximidamide], hydrochloride (1:2)

A mixture of 3-amidinobenzaldehyde hydrochloride (3.2 g, 17 mmol) and tetrahydro-4H-tiapyran-4-one (928 mg, 8 mmol) in 12 ml of 85% phosphoric acid is heated in an oil bath at 100° for two hours. The cooled mixture is triturated with ether (5×100 ml) and with 1:1 ether/methanol (200 ml). The residue is dissolved in 200 ml of hot methanol, filtered and concentrated in vacuo. The residue is treated with water to precipitate 1.7 g (mp>400°) of crude product (phosphoric acid addition salt). This material, suspended in ether, is treated with dry HCl gas for 5 minutes. After standing for 24 hours, the product is collected to give 1.3 g, m.p. 200° d. Recrystallization from 10 ml of water gives 820 mg (22%) of product, m.p. 225° d.

EXAMPLE 2

4,4'-[(4-Oxo-2H-thiopyran-3,5-(4H,6H)diylidene)dimethylidyne]bis[benzenecarboximidamide], hydrochloride (1:2)

A. 4-Amidinobenzaldehyde hydrochloride Ref: E. German Pat. No. 109,864; Farmdoc 11059W.

To a solution of 4-cyanobenzaldehyde (10 g, 0.076 mole) in dioxane (30 ml), $Et_2O$ (11 ml) and MeOH (7.2 g) (all solvents dried before use) is added dry HCl gas (21.2 g, passed through two $H_2SO_4$ towers) at ice bath temperature. The solution is left at 0°–5° for 92 hours, then poured into 200 ml of Et$_2$O and stirred for 1 hour. The iminoether hydrochloride is collected and washed with ether, then dissolved in 75 ml H$_2$O, made alkaline with 10% NaOH and extracted with ether (2×). The extracts are washed with saturated brine (2×), dried (MgSO$_4$) and concentrated in vacuo to give 9.2 g of semi-solid iminoether free base.

The iminoether is dissolved in 100 ml MeOH and treated with 34 ml of 10% aqueous NH$_4$Cl and heated at 90° (oil bath) for 2 hours. The cooled mixture is poured into 400 ml Et$_2$O; the oil that separates is diluted with 40 ml MeOH and poured into 400 ml acetone. The precipitate that forms (1.73 g, NH$_4$Cl) is removed by filtration and the filtrate is diluted with another 200 ml acetone, whereupon product precipitates to give 2.9 g, m.p. 195°–220°. The filtrate, after concentration in vacuo to remove MeOH and H$_2$O, is treated again with acetone, giving an additional 3.81 g, m.p. 210°–220°. The combined product is stirred with ethereal HCl for 1 hour, filtered and washed with fresh ether to give 6.7 g, m.p. 211°–212°.

B. 4,4′-[(4-Oxo-2H-thiopyran-3,5(4H,6H)-diylidene)-dimethylidyne]bis[benzenecarboximidamide], hydrochloride (1:2)

A mixture of 4-amidinobenzaldehyde hydrochloride (1.0 g, 5.4 mmol) and tetrahydro-4H-thiopyran-4-one (0.3 g, 2.6 mmol) in 5 ml of water containing 1 ml of concentrated hydrochloric acid is heated at reflux temperature for 2 hours, during which time product precipitates. After cooling, the product is collected and dried in vacuo over P$_2$O$_5$ to give 840 mg (67%) of product, m.p. 312°–313° d. Recrystallization of an analytical sample from a small amount of water gives material, m.p. 300° d.

EXAMPLE 3

3,3′-[(4-Oxo-2H-thiopyran-3,5(4H,6H)diylidene)dimethylidyne]bis[benzenecarboximide], S,S-dioxide, hydrochloride (1:2)

A mixture of 3-amidinobenzaldehyde hydrochloride (4.0 g, 22 mol) and tetrahydro-4H-thiopyran-4-one, 1,1-dioxide (1.48 g, 10 mmol) in 12 ml of 85% phosphoric acid is heated at 100° for 2 hours. The cooled product is poured into 4 volumes of methanol and left at 5° overnight. The crude product (3.24 g) is suspended in methanol, treated with dry HCl gas for 15 minures and left at 5° overnight. The product is precipitated with a large volume of ether to give 2.5 g of crude product. Recrystallization from water gives 930 mg (18%) of product, m.p. >400°.

EXAMPLE 4

4,4′-[(4-Oxo-2H-thiopyran-3,5(4H,6H)diylidene)dimethylidyne]bis[benzenecarboximidamide]hydrochloride (1:2)

A mixture of 4-amidinobenzaldehyde hydrochloride (3.7 g, 20 mmol) and tetrahydrothiopyran-4-one, 1,1-dioxide (1.48 g, 10 mmol) in 15 ml of 85% phosphoric acid is heated at 100° for 2 hours. The mixture is cooled and diluted with 1:1 MeOH/Et$_2$O (150 ml). The product that separates is collected and washed with methanol/ether (1:1) and ether and is dried in vacuo over KOH at 60° to give 2.76 g, m.p. >300°.

The crude product is suspended in methanol and is treated with dry HCl gas at 0° for 20 minutes and left overnight at 5°. The product is collected to give 2.35 g, m.p. >400°. Trituration with methanol gives 2.05 g (41%) of product, m.p. >400°.

EXAMPLES 5 to 15

Using the procedure described in Example 2 and employing the benzaldehyde derivatives in Column I and the cyclic ketone derivatives in Column II, there is obtained the product in Column III (Table I).

TABLE I

| Ex. No. | Column I | Column II | Column III |
|---|---|---|---|
| 5. | 4-(CH$_3$NH-C(=NH))-C$_6$H$_4$-CHO · HCl | tetrahydro-4H-pyran-4-one | 3,5-bis[(4-(CH$_3$NH-C(=NH))phenyl)methylene]-tetrahydro-4H-pyran-4-one · 2HCl |
| 6. | 3-(C$_6$H$_5$NH-C(=NH))-C$_6$H$_4$-CHO · HCl | 1-benzyl-piperidin-4-one | 3,5-bis[(3-(C$_6$H$_5$NH-C(=NH))phenyl)methylene]-1-benzyl-piperidin-4-one · 3HCl |
| 7. | 4-[(3-CF$_3$-C$_6$H$_4$)NH-C(=NH)]-C$_6$H$_4$-CHO · HCl | 1-acetyl-pyrrolidin-4-one (3-CF$_3$ substituted) | 3,5-bis[(4-[(3-CF$_3$-C$_6$H$_4$)NH-C(=NH)]phenyl)methylene]-1-acetyl-piperidin-4-one · 2HCl |

TABLE I-continued
| Ex. No. | Column I | Column II | Column III |
|---|---|---|---|
| 8. | | | |
| 9. | | | |
| 10. | | | |
| 11. | | | |
| 12. | | | |
| 13. | | | |
| 14. | | | |
| 15. | | | |
What is claimed is:
1. A compound of the structure
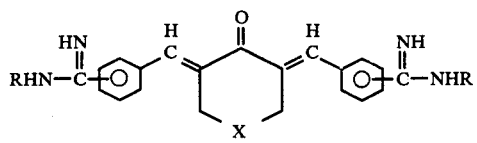
wherein X is S, SO₂, O or NR¹, R is H, lower alkyl or aryl, and R¹ is H, lower alkyl, lower alkanoyl, aroyl or aryl-lower alkyl, or acid-addition salts thereof.
2. The compound as defined in claim 1 wherein the
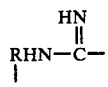

group is in the meta or para position.

3. The compound as defined in claim 1 wherein R is H or lower alkyl.

4. The compound as defined in claim 1 wherein X is S or $SO_2$.

5. The compound as defined in claim 1 having the name 3,3'-[(4-oxo-2H-thiopyran-3,5-(4H,6H)diylidene)-dimethylidyne]bis[benzenecarboximidamide], or its hydrochloride salt.

6. The compound as defined in claim 1 having the name 4,4'-[(4-oxo-2H-thiopyran-3,5-(4H,6H)diylidene)-dimethylidyne]bis[benzenecarboximidamide], or its hydrochloride salt.

7. The compound as defined in claim 1 having the name 3,3'-[(4-oxo-2H-thiopyran-3,5-(4H,6H)diylidene)-dimethylidyne]bis[benzenecarboximidamide]S,S,-dioxide or its hydrochloride 8. The compound as defined in claim 1 having the name 4,4'-[(4-oxo-2H-thiopyran-3,5-(4H,6H-diylidene)-dimethylidyne]bis[benzenecarboximidamide]S,S-dioxide or its hydrochloride salt.

9. An anti-inflammatory composition comprising a therapeutically effective amount of a compound as defined in claim 1 in a physiologically acceptable carrier therefor.

10. A method for treating an inflammatory condition in a mammalian host, which comprises administering an effective amount of the composition as defined in claim 9.

* * * * *

UNITED STATES PATENT AND TRADEMARK OFFICE
CERTIFICATE OF CORRECTION

PATENT NO. : 4,325,958
DATED : April 20, 1982
INVENTOR(S) : George C. Rovnyak

It is certified that error appears in the above—identified patent and that said Letters Patent is hereby corrected as shown below:

Column 1, line 37-40, the structure should read
$$-- RHN-\overset{\overset{HN}{\|}}{C}- --.$$

Column 4, line 55, "1.3" should read --1.13--.
Column 5 and 6, Table 1, Ex. 7, Column II, the structure should read --

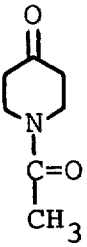

--.

Column 8, lines 64-66, the structure should read
$$-- RHN-\overset{\overset{HN}{\|}}{C}- --.$$

Signed and Sealed this

Twenty-fourth Day of August 1982

|SEAL|

Attest:

GERALD J. MOSSINGHOFF

Attesting Officer          Commissioner of Patents and Trademarks